United States Patent [19]

Samour

[11] Patent Number: 4,910,020
[45] Date of Patent: Mar. 20, 1990

[54] TRANSDERMAL MEDICATOR

[75] Inventor: Carlos Samour, Wellesley, Mass.

[73] Assignee: Macrochem Corporation, Billerica, Mass.

[21] Appl. No.: 260,993

[22] Filed: Oct. 21, 1988

[51] Int. Cl.[4] .......................................... A61F 13/02
[52] U.S. Cl. .................................. 424/448; 424/449; 424/447
[58] Field of Search .................. 424/447, 448, 449

*Primary Examiner*—Ellis P. Robinson
*Assistant Examiner*—Leon R. Horne
*Attorney, Agent, or Firm*—N. Blumenkopf

[57] ABSTRACT

A transdermal medication device for applying medication on the skin of the user comprising upper and lower layers having cooperating filaments for detachably securing the upper layer to the lower layer. The lower layer has an opening therethrough, the upper layer carrying a medication reservoir which seats in the opening. In one form of the invention, the device is a patch attached by pressure-sensitive adhesive to the skin. In another form of the invention, the lower layer is a band for attaching the device about the chest, waist, arm or leg of the user.

10 Claims, 2 Drawing Sheets

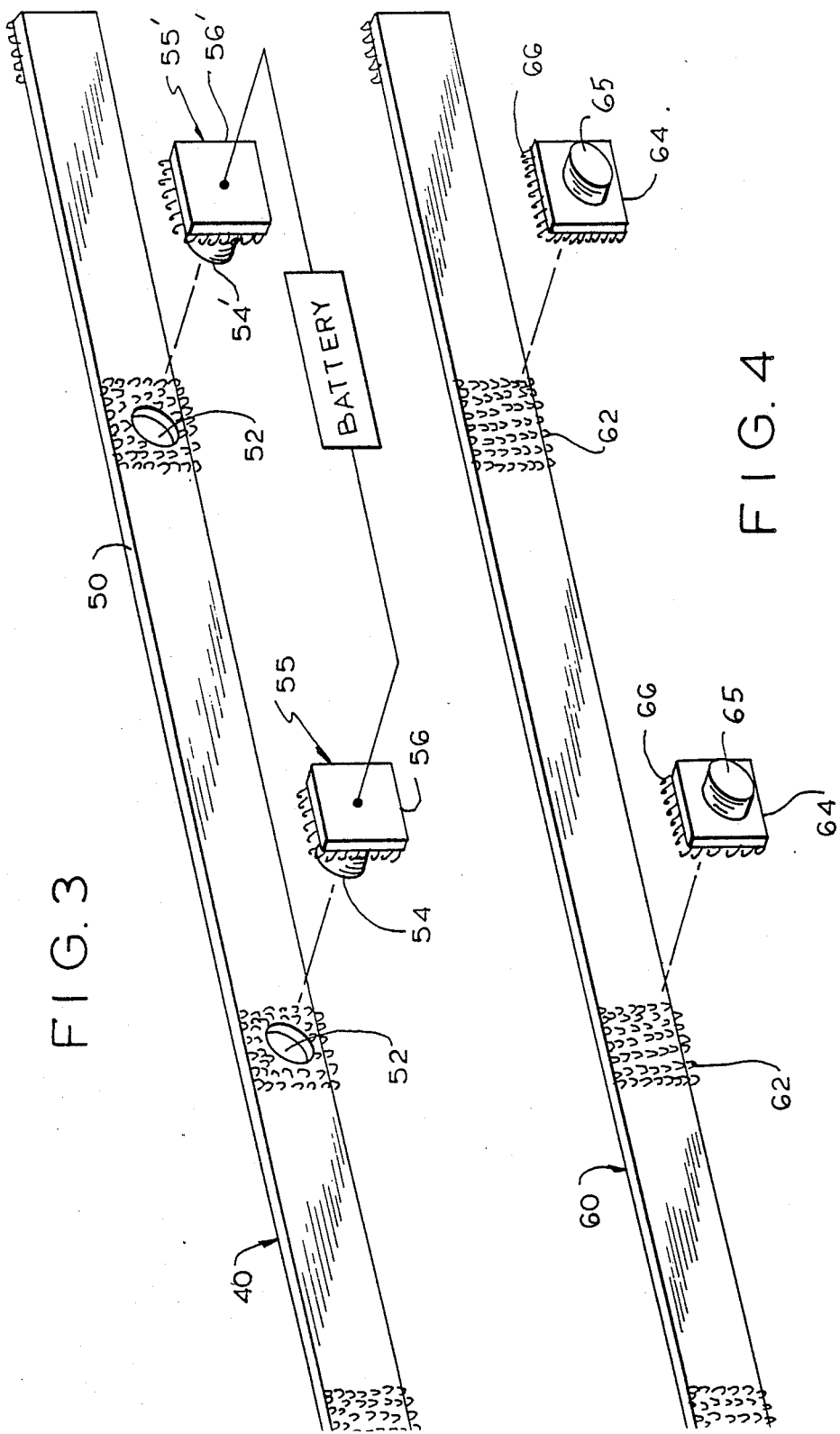

TRANSDERMAL MEDICATOR

BACKGROUND OF THE INVENTION

1. Field of the Invention

This invention relates to therapeutic appliances and, more particularly, to a transdermal drug-delivery device.

2. State of the Prior Art

Transdermal drug-delivery patches are currently being prescribed for the treatment of various medical problems, such as angina and motion sickness. Advantages of such devices include zero-order delivery or controlled delivery and stoppage of delivery in the event of an adverse reaction; in this case the patient stops delivery of the drug to th body abruptly by removing the device containing the drug reservoir. Depending on the drug, when a transdermal patch or vehicle (e.g. an ointment containing a drug) is removed, the skin may serve as a reservoir for continued delivery of the drug to the body. When the supply of the drug in the device is exhausted, the device is removed and a new one is applied to the skin. Transdermal patches are attached to the skin by means of a pressure-sensitive adhesive layer. Adhesives in current use, however, cling so aggressively that their removal can cause skin irritation and even trauma. To avoid this problem, the next patch is most often applied to a different, but equivalent, area of skin. For a period of time thereafter blood concentrations of the drug can vary anywhere from zero-order to the steady-state blood level. If the new patch is applied to the same area of the skin as that used previously, however, steady-state diffusion already exists and zero-order delivery should continue without interruption.

Since patients who use transdermal delivery patches regularly experience trauma consistently when the patches are removed, understandably, this problem becomes magnified when larger doses are required. In this case, correspondingly larger patches are needed and, of course, cover a more extensive area of skin.

U.S. Pat. No. 3,734,097 discloses a therapeutic adhesive tape of the type previously described which is especially adapted for the treatment of skin lesions.

In U.S. Pat. No. 3,742,951, there is disclosed a bandage for controlled release of medications, such as vasodilators.

U.S. Pat. No. 4,297,995 discloses the use of a two-piece medical bandage employing a post and a base.

SUMMARY OF THE INVENTION

The present invention involves a two-piece transdermal device having a lower member attached to the skin by adhesive or otherwise applied to the body and an upper member containing the drug to be applied. The lower segment includes an aperture through which the drug of the upper member can contact the skin. Fastening means, such as "Velcro" as described in U.S. Pat. No. 2,717,437, or snap clips, screw-type attachments or the like, are used to detachably secure the upper member to the lower member, eliminating the necessity of removal of the lower member from the body and giving rise to the major advantage of providing continuous medication to the same area of the skin while reducing trauma to that skin area.

As an example, a device utilizing the "Velcro" system would consist of a patch with a release paper, a pressure-sensitive adhesive coated on the back side of a rectangular square, and a circular or oval form of the "Velcro" locks. In the first part of the device, the center of the patch is open to allow the drug-containing part of the device to come in contact with the skin. The size of the opening is determined by the area of the skin to which the drug will be delivered The second part of the device consists of an impermeable film laminated to the "Velcro" loop segment and contains the drug-delivery system in the center. This is placed on the patch segment with the drug-containing portion in contact with the skin. "Velcro" parts are interlocking and thus hold the drug portion of the device in place against the skin. When the device is exhausted of the drug, e.g. a day later, the drug portion of the device is removed by dis-interlocking the "Velcro" loops from the hooks. A new drug segment is then placed in the area of skin that had been used previously. When this is exhausted, it is removed and a third one is put in its place. This is then continued for the prescribed number of times, when the old patch is removed and a new one placed on another part of the body.

Another approach that is contemplated (that does not utilize a pressure-sensitive adhesive) involves an elastic device that can be applied around part of the body, such as the arm, chest or leg. This part of the device contains an area, or several areas, wherein the drug-delivery portion is applied as in the patch case. In this case, one can remove the anchoring device without irritating the skin. If desired, one could remove the whole device which is held together around the arm, chest or leg by means of "Velcro" fasteners. If desired, one could then apply the delivery system in exactly the same place or in a different location by simply rotating the device or placing it in a different location.

Instead of using a "Velcro" fastener system, one could employ an interlocking, screw-type system. or alternatively, an adhesive (e.g. a pressure-sensitive adhesive) means.

BRIEF DESCRIPTION OF THE DRAWINGS

FIG. 3 is a plan view of a transdermal therapeutic device according to one form of the invention;

FIG. 4 is a plan view of a transdermal therapeutic device according to another form of the invention.

Figure 1:
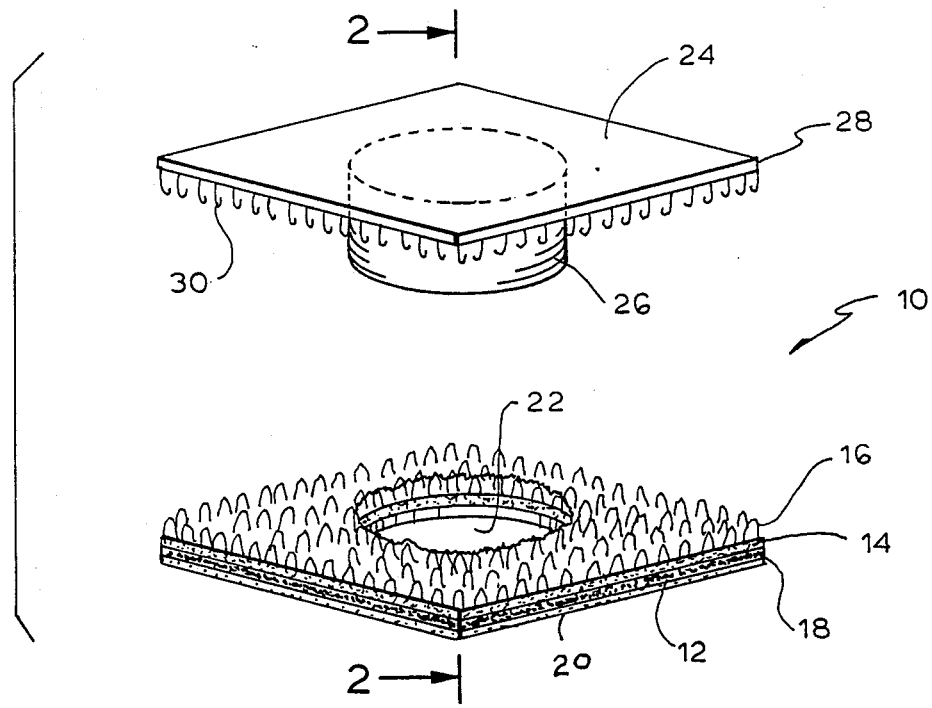
FIG. 1 is an exploded perspective view of a transdermal patch according to the present invention.
Figure 2:
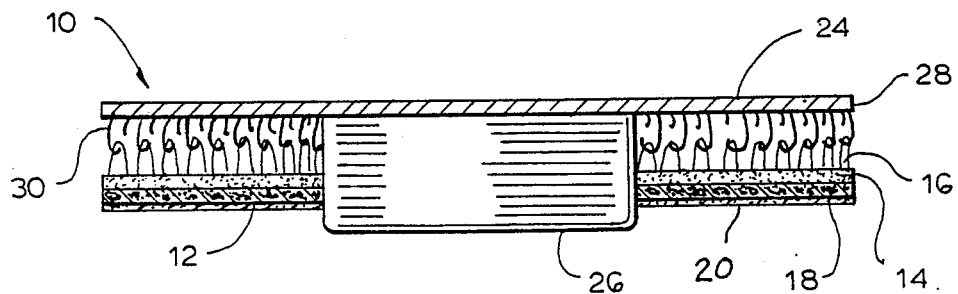
FIG. 2 is a sectional view taken along the plane of line 2—2 in FIG. 1.

DETAILED DESCRIPTION OF THE INVENTION with continuing reference to the accompanying drawings, wherein like reference numerals designate similar parts throughout the various views, reference numeral 10 generally designates transdermal medication application patch according to a preferred form of the invention, as illustrated primarily in FIGS. 1 and 2.

The patch 10 comprises a lower member 12. This lower member 12 includes a base 14 of a material sold under the trade name of "Velcro" having hook-like filaments 16 rising therefrom. A pressure-sensitive adhesive 18 is coated on the bottom of the "Velcro" base. A release sheet 20 underlies the adhesive coating 18. The member 12 has a central opening 22 of predetermined size depending on the type and amount of medication prescribed.

An upper member 24 has a reservoir 26 depending from the "Velcro" strip 28 which has filaments 30 cooperative with the filaments 16 to detachably secure th upper member 28 to the lower member 12. The precise construction of the medication reservoir 26 is dependent on the medication prescribed and is generally of a frangible or openable material so that the medication can reach the skin through opening 22.

In use, the transdermal patch is applied on the desired area of skin after the release sheet has been removed. Then, after the prescribed period of usage, the upper layer is pulled free and replaced one or more time with another upper layer containing a new reservoir of medication.

In the embodiments of FIGS. 3 and 4, in lieu of adhesive a belt 40, which may be at least in part elastic, is provided with "Velcro" ends 42 for adjustably attaching the belt 40 about the arm, leg, waist, chest, thigh or other selected portion of the body.

In the form of the invention of FIG. 3, the device includes a lower member 50 having one or more openings 52 into which the reservoir or reservoirs 54 for medication extend. The reservoirs 54 are carried by an upper member 56. The lower member 50 and upper member 56 are detachably secured to each other by cooperating "Velcro" filaments. The entire length of the belt 40 may be made, if desired, of "Velcro" and the medication is applied and renewed in the same manner as heretofore described.

Indicated in FIG. 3 is a well-known iontophoretic medicating system wherein a source of electricity and the two electrodes 55 and 55' (one or both containing medication in the elements 54 and 54') re used in place of the usual form of medication present in the reservoir 26 (FIG. 1).

In the form of the invention shown in FIG. 4, a belt (upper member) 60 is provided with "Velcro" ends & one or more "Velcro" attaching means 62. The medication applying means 64 (in this case the lower element) is secured to the corresponding cooperating means 62 by similar "Velcro" means 66. In this form of the invention the upper member belt provides pressure and securement means for the medication applying element 64. Reservoirs 65 for medication are similar to reservoirs 26.

What is claimed is:

1. A transdermal medication device comprising a lower layer, means for attaching the lower layer over the skin of a patient, said lower layer having a medication receiving opening therethrough, an upper layer having a reservoir for medication depending therefrom, said reservoir seating in said opening, and means detachably connecting said upper and lower layers together.

2. A device according to claim 1, wherein said means detachably connecting said upper layer to said lower layer comprises cooperating filaments.

3. A device according to claim 1, wherein said lower layer comprises a cloth having hook-like filaments woven therewith, said upper layer being of cloth having filaments woven therein, said filaments of said upper layer cooperating with the filaments of said lower layer to form said means detachably securing said upper layer to said lower layer.

4. A device according to claim 1, wherein said device is in the form of a patch, said means for attaching said lower layer on the skin being a pressure-sensitive adhesive coating underlying said lower layer.

5. A device according to claim 1, wherein said means detachably connecting said upper layer to said lower layer comprises cooperating filaments, said lower layer having a coating of pressure-sensitive adhesive on the lower surface thereof forming said means for attaching said lower layer to the skin.

6. A device according to claim 1, wherein said lower layer comprises a cloth having hook-like filaments woven therewith, said upper layer being of cloth having filaments woven therein, said filaments of said upper layer cooperating with the filaments of said lower layer to form said means detachably securing said upper layer to said lower layer, said means detachably connecting said upper layer to said lower layer comprising cooperating filaments, sad lower layer having a coating of pressure-sensitive adhesive on the lower surface thereof forming said means for attaching said lower layer to the skin.

7. A transdermal medication device comprising a lower layer, means for attaching the lower layer over the skin of a patient, said lower layer having a medication-receiving opening therethrough, an upper layer having a reservoir for medication depending therefrom, said reservoir seating in said opening, means detachably connecting said upper and lower layers together, said lower layer comprising an elongated band for attachment about a body portion of a patient.

8. A device according to claim 7, including cooperating filaments on the ends of said band for attachment to each other forming said means for securing said lower layer on the skin of the user.

9. A device according to claim 7, wherein said means detachably connecting said upper layer to said lower layer comprises cooperating filaments.

10. A device according to claim 7, wherein said lower layer comprises a cloth having hook-like filaments woven therewith, said upper layer being of cloth having filaments woven therein, said filaments of said upper layer cooperating with the filaments of said lower layer to form said means detachably securing said upper layer to said lower layer.

* * * * *